(12) United States Patent
DuBois et al.

(10) Patent No.: US 6,448,437 B1
(45) Date of Patent: Sep. 10, 2002

(54) DISPROPORTIONATION CATALYST

(75) Inventors: Donn Anthony DuBois; Brendan Dermot Murray, both of Houston, TX (US)

(73) Assignee: Mossi & Ghisolfi Overseas S.A., Luxemborg (LU)

( * ) Notice: Subject to any disclaimer, the term of this patent is extended or adjusted under 35 U.S.C. 154(b) by 69 days.

(21) Appl. No.: 09/643,398

(22) Filed: Aug. 22, 2000

Related U.S. Application Data

(60) Provisional application No. 60/151,529, filed on Aug. 30, 1999.

(51) Int. Cl.[7] ............................................. C02C 51/347
(52) U.S. Cl. ...................................................... 562/481
(58) Field of Search ......................................... 562/481

(56) References Cited

U.S. PATENT DOCUMENTS

| | | |
|---|---|---|
| 2,823,231 A | 2/1958 | Raeke et al. |
| 2,833,816 A | 5/1958 | Saffer et al. |
| 2,849,482 A | 8/1958 | Raecke et al. |
| 3,546,282 A | 12/1970 | Tamotsu et al. |
| 3,766,258 A * | 10/1973 | Engelbrecht et al. |
| 3,870,754 A | 3/1975 | Yamashita et al. |
| 4,820,868 A * | 4/1989 | Mitamura et al. |
| 4,933,491 A | 6/1990 | Albertins |
| 4,950,786 A | 8/1990 | Sanchez et al. |
| 5,081,252 A * | 1/1992 | Mitamura et al. |

FOREIGN PATENT DOCUMENTS

| | | | |
|---|---|---|---|
| GB | 1389130 | * | 4/1975 |
| JP | 42-9136 | * | 6/1967 |

* cited by examiner

*Primary Examiner*—Paul J. Killos
(74) *Attorney, Agent, or Firm*—Renner, Kenner, Greive, Bobak, Taylor & Weber

(57) ABSTRACT

Disclosed are halide-free catalyst compositions for the disproportionation/isomerization of aromatic carboxylic acid salts. In one embodiment the catalyst comprises a mixed catalyst of compounds of copper, zinc, and zirconium; and, in a second embodiment, the catalyst comprises a copper compound treated with a base, optionally used with a promoter. Both halide-free catalysts provide advantages with respect to metallurgic problems, as well as good stability, activity and selectivity, and the later is faster kinetically at lower temperatures.

25 Claims, No Drawings

DISPROPORTIONATION CATALYST

CROSS REFERENCE

This application claims the benefit of U.S. Provisional Application No. 60/151,529, filed Aug. 30, 1999, the entire disclosure of which is hereby incorporated by reference.

This application is related to U.S. application Ser. Nos. 60/151,577, 60/151,607, 60/151,498, 60/151,602, 60/151,603, 60,151,489, 60/151,604, 60/151,606, 60/151,589, 60/151,497, 60/151,590, 60/151,578 filed of even date.

FIELD OF THE INVENTION

This invention is generally related to the disproportionation/isomerization of salts of aromatic carboxylic acids. More particularly, this invention is related to catalysts used in the disproportionation/isomerization of salts of aromatic carboxylic acids. The present invention provides halide-free, copper based catalyst alternatives to the metal halide catalysts typically used in the art for disproportionation reactions. The catalysts demonstrate particularly good yields and high selectivity in the disproportionation of potassium naphthoate to the potassium salts of 2,6 NDA. In one embodiment the catalyst comprises a mixed catalyst of compounds of copper, zinc, and zirconium; and, in a second embodiment, the catalyst comprises a copper compound treated with a base, used with an alkali metal promoter. The halide-free catalysts of this invention provide good stability, activity, and selectivity in a disproportionation/isomerization reaction.

BACKGROUND OF THE INVENTION

It is known in the art that aromatic carboxylic acids are useful as raw materials for the production of polyesters for fibers, films and plasticizers. One method for making aromatic carboxylic acids is oxidation. An alkyl or acyl substituted aromatic compound is converted to the corresponding aromatic carboxylic acid using a heavy metal catalyst in the liquid phase. For example, U.S. Pat. Nos. 2,833,816; 3,870, 754; 4,933,491; and 4,950,786 disclose methods for making naphthlene dicarboxylic acid by oxidation.

In another method, naphthalene monocarboxylic acid and naphthalene dicarboxylic acids other than 2,6-naphthalene dicarboxylic acid can be converted to 2,6-naphthalene dicarboxylic acid using a disproportionation/isomerization reaction, the so called Henkel rearrangement reaction. Henkel and Cie first patented the reaction of naphthoic acid salts to 2,6-naphthalene dicarboxylic acid in the late 1950s. (See U.S. Pat. Nos. 2,823,231 and 2,849,482.)

The Henkel and Cie patents, as well as many other references in the prior art teach the preferential use of cadmium halide, as well as other metal halides as catalysts in disproportionation reactions.

U.S. Pat. No. 3,546,282 discloses the use of iron, zinc, cadmium, and copper oxides, however the examples demonstrate cadmium salts were the most effective.

One patent that takes another view is U.S. Pat. No. 3,766,258 that teaches the use of a catalyst composition consisting of basic copper carbonate, cadmium fluoride and potassium carbonate. At Col. 1, line 60, it is stated the invention is particularly useful in a process for making terephthalic acid from a metallic salt of benzoic acid. In the examples water extraction and subsequent acidification/filtration isolate the products. No analytical technique is disclosed, and it is likely unreacted potassium napthoate is mistakenly counted as a diacid product. In the present invention, it is demonstrated in Ex. 10 that basic copper carbonate which has not been treated as taught in the present invention promotes a deleterious side reaction.

It would provide a significant improvement in the art if there were available a disproportionation/isomerization catalyst which affords good selectivity to the 2,6-isomer of the potassium salt of naphthalene dicarboxylic acid without the extreme toxicity and reactor corrosion concerns which are typical of the heavy metal halides currently accepted in the art.

The present invention provides effective, halide-free catalysts for a disproportionation reaction.

SUMMARY

In accordance with the foregoing, the present invention provides the option of two very effective halide-free disproportionation/isomerization catalysts, the first comprising a copper compound, a zinc compound, and at least one compound selected from the group consisting of aluminum, zirconium, magnesium, a rare earth, and mixtures thereof. The first embodiment is exemplified by a catalyst comprising sintered copper (II) carbonate, zinc carbonate, and zirconium carbonate. Another embodiment is a catalyst comprising a copper compound that is treated with a base and optionally used with a promoter. The second embodiment is exemplified by a catalyst comprising copper (II) carbonate treated with potassium hydroxide, optionally with a cesium carbonate promoter. The copper (II)-based catalyst with a cesium carbonate promoter has been demonstrated to be kinetically faster at lower temperatures. Specific examples demonstrate good yields and high selectivity in the disproportionation of naphthoic acid salts to 2,6-naphthalene dicarboxylic acid, using the catalysts of this invention.

DETAILED DESCRIPTION OF THE INVENTION

Starting materials for a disproportionation in which the catalyst of the invention is useful include salts of aromatic mono-, di-, or polycarboxylic acids. Such acids include, for example, benzoic acid, $\alpha$- and $\beta$-naphthoic acid, diphenyl monocarboxylic acids, as well as phthalic acid, isophthalic acid, terephthalic acid, naphthalic acid and other naphthalene dicarboxylic acids or diphenic acid and other diphenyl dicarboxylic acids. In addition, mono- or dicarboxylic acids in which the carboxylic groups are attached to another aromatic ring system, for example to anthracene, terphenyl, diphenyl methane or benzophenone radicals, are suitable for use as starting materials for the process of the invention, as well as tri- and polycarboxylic acids which are derived from aromatic ring systems. Also, mixtures of such acids which are formed, for example, by oxidation, or mixtures of alkyl aromatic compounds may be used.

The starting materials may also be salts of monobasic heterocyclic carboxylic acids, the carboxyl groups of which are attached to heterocyclic rings having an aromatic structure. Such acids are derived, for example, from pyridine, pyrazine, pyrimidine, pyridazine, $\alpha$-pyran, furan, thiophene, thiazole, quinoline, isoquinoline, indole, benzotriazole and benzimidazole.

In all of these carboxylic acids the aromatic ring or the heterocyclic ring having an aromatic structure can, in addition to the carboxyl group, also carry other substituents such as halogen atoms or alkyl radicals, provided that they do not decompose at temperatures below the reaction temperature. The term aromatic carboxylic acid is intended to include both compounds having a homocyclic aromatic ring and compounds having a heterocyclic ring.

When aromatic monocarboxylic acids are used as starting materials for a disproportionation reaction, the reaction products obtained are industrially valuable dicarboxylic acids or the salts thereof, such as, for example, terephthalic acid and 2,6-naphthalene dicarboxylic acid. Aromatic monocarboxylate includes benzoate, methyl benzoate, naphthoate, and similar compounds.

It is advantageous to use the above-mentioned carboxylic acids in the form of an alkali metal salt. Preferably the potassium salts or the sodium salts are used. The lithium, rubidium and cesium salts, may be used, but generally are not for reasons of economy. It is also possible to use mixtures of salts of two different metals. Reaction materials that form the above-mentioned salts may also be used.

Suitable temperatures for the disproportionation reaction are in the range of from about 340° C. to 500° C. Better results are observed where the temperature is from about 400° C. to 480° C. The preferred temperature is from about 440° C. to 460° C. This temperature range is, however, very limited. Raising the temperature generally improves conversion, however decomposition through decarboxylation and tarring becomes more severe at higher temperatures. Generally, at temperatures over 500° C. the decomposition of the organic material and product become substantial and lead to carbonization, so temperatures this high for very long periods of time should be avoided.

The disproportionation reaction is carried out under the pressure of gaseous carbon dioxide. The gaseous mixture may contain an inert gas or gases such as nitrogen, methane, or other gaseous paraffinic, olefinic, and aromatic hydrocarbons. In the case of a gas mixture, $CO_2$ is preferably present as at least about 10% of the mixture. The presence of oxygen should be avoided due to the fact that it can affect the yields. Suitable $CO_2$ pressures are from about 200 to 10,000 psig. Actual pressures depend upon the partial pressures of other gases present. A more preferred $CO_2$ pressure range is from about 350 to 1100 psig. To accelerate the reaction and suppress the occurrence of side reactions the reaction temperature is preferably about 450° C. and the pressure is about 850 psig to 950 psig.

The reaction medium or dispersant may be any compound with sufficient thermal stability. It is not restricted to aromatic compounds, however aromatic compounds are suitable. Examples of suitable solvents include a single compound or mixture of compounds selected from a variety of aprotic polycyclic aromatic compounds, such as, for example, naphthalene, methylnaphthalene, dimethylnaphthalene, diphenyl ether, dinaphthyl ether, terphenyl, anthracene, phenanethrene, and mixtures thereof. The polycyclic aromatic compound is used in an amount of 1 to 6 times, preferably 2 to 4 times, the amount of the starting material based on weight.

The presence of water should be avoided in the reaction system. In addition, it is desirable to eliminate oxygen from the system as far as possible.

In the first embodiment of the present invention the disproportionation/isomerization catalyst comprises mixtures of a copper compound, a zinc compound, and at least one compound selected from the group consisting of aluminum, zirconium, magnesium, and a rare earth, and mixtures thereof.

The copper content of the catalyst can vary over a wide range for example, from about 10 percent by weight to about 80 percent by weight, calculated as the oxide, basis the total weight of the catalyst. However, for an optimal combination of initial catalyst activity and catalyst stability, a copper content in the range of from about 25 percent by weight to about 75 percent by weight, calculated as the oxide, is preferred, especially from about 30 percent by weight to about 70 percent by weight, calculated as the oxide. All ratios specified herein are metal atoms unless otherwise noted.

The zinc content of the catalyst is typically in the range of from about 10 percent by weight to about 80 percent by weight, calculated as the oxide, basis the total weight of the catalyst. Preferably, the zinc content of the catalyst is in the range of from about 15 percent by weight to about 75 percent by weight, calculated as the oxide, especially from about 20 percent by weight to about 70 percent by weight, calculated as the oxide. The ratio of zinc to copper in the catalyst is generally in the range of from about 1:5 to about 5:1, and preferably in the range of from about 1:4 to about 2:1.

The catalyst additionally comprises at least one compound selected from the group consisting of aluminum, zirconium, magnesium, a rare earth and mixtures thereof.

When a rare earth compound is utilized, the rare earth content of the catalyst is typically in the range of from about 0.1 percent by weight to about 20 percent by weight, calculated as the oxide, basis the total weight of the catalyst. Preferably, the rare earth content of the catalyst is in the range of from about 0.2 percent by weight to about 15 percent by weight, calculated as the oxide, especially from about 0.3 percent by weight to about 10 percent by weight, calculated as the oxide.

As used herein, the terms "rare earth" and "lanthanide" refer to the series of elements with atomic numbers ranging from 57 (lanthanum) through 71 (lutetium). With regard to the rare earth (lanthanide) series, mixed metals are readily available commercially. For purposes of the present invention, the rare earth is selected from the group consisting of praseodymium, neodymium, yttrium, lanthanum, samarium, thorium, cerium and mixtures thereof, with lanthanum being preferred.

When the catalyst contains aluminum, the aluminum content of the catalyst is typically in the range of from about 0.05 percent by weight to about 30 percent by weight, calculated as the oxide, basis the total weight of the catalyst. Preferably, the aluminum content of the catalyst is in the range of from about 0.4 percent by weight to about 20 percent by weight, calculated as the oxide, especially from about 0.6 percent by weight to about 10 percent by weight, calculated as the oxide.

When the catalyst contains zirconium, the zirconium content of the catalyst is typically in the range of from about 0.05 percent by weight to about 30 percent by weight, calculated as the oxide, basis the total weight of the catalyst. Preferably, the zirconium content of the catalyst is in the range of from about 0.4 percent by weight to about 20 percent by weight, calculated as the oxide, especially from about 0.6 percent by weight to about 10 percent by weight, calculated as the oxide.

When the catalyst contains magnesium, the magnesium content of the catalyst is typically in the range of from about 0.05 percent by weight to about 30 percent by weight, calculated as the oxide, basis the total weight of the catalyst. Preferably, the magnesium content of the catalyst is in the range of from about 0.4 percent by weight to about 20 percent by weight, calculated as the oxide, especially from about 0.6 percent by weight to about 10 percent by weight, calculated as the oxide.

When mixtures of a rare earth and/or aluminum and/or zirconium and/or magnesium are utilized, the total amount present in the catalyst is typically in the range of from about 0.05 percent by weight to about 30 percent by weight, calculated as the oxide, basis the total weight of the catalyst. Preferably, the total amount present in the catalyst is in the range of from about 0.4 percent by weight to about 20 percent by weight, calculated as the oxide, especially from about 0.6 percent by weight to about 10 percent by weight, calculated as the oxide.

In one embodiment, the catalyst comprises copper, zinc and zirconium. In another embodiment, the catalyst comprises, copper, zinc and aluminum. In another embodiment, the catalyst comprises copper, zinc, aluminum and zirconium. In another embodiment, the catalyst comprises copper, zinc and a rare earth. In another embodiment, the catalyst comprises copper, zinc, magnesium and a rare earth. The catalyst may also comprise a specially treated copper compound optionally used with a promoter compound selected from alkali metal compounds.

Various procedures can be utilized to prepare the catalysts of the present invention. For example, individual solutions of the metals may be prepared and mixed together followed by the addition of an aqueous alkaline solution. Alternatively, a first aqueous solution comprising a copper or zinc salt and a second solution comprising a soluble base and at least one soluble salt of at least one second metal can be prepared, and these two solutions are then added simultaneously to a vessel containing water. In a preferred embodiment, the catalysts are prepared by co-precipitating from aqueous solution thermally decomposable compounds of copper, zinc, and rare earth and/or aluminum and/or zirconium and/or magnesium, washing the precipitate and calcining the precipitate to give the metal oxides. The catalyst precursor is subjected to a reduction treatment to give the active catalyst.

It is understood that the catalyst is usually handled and stored in the form of its precursor, which indeed is referred to in commerce as the "catalyst", although it is not the catalyst in the strict sense of the agent taking part in chemical reactions such as disproportionation/isomerization. Reduction of the precursor to the catalyst is normally carried out by the operator of the chemical process. The precursor may be in shapes, e.g., pellets, as required by the user of the catalyst, or may be in its condition before the shaping operation, e.g., as powder or lightly compressed powder.

The initial form in which the copper, zinc and rare earth and/or aluminum and/or zirconium and/or magnesium are employed is the oxide, although compounds which are readily converted to the oxide, e.g., the corresponding metal carbonates, are also suitable initially employed as these are converted to the oxide during pretreatment subsequent to the formation of the initially prepared catalyst composition. Pretreatment of the catalyst in hydrogen and operation of the catalyst in the reaction environment will cause at least partial reduction of some of the metals, such as copper, to lower oxidation states, and it is intended that catalysts with these reduced states will fall within the scope of this invention.

In the method of making the catalyst the reaction conditions for the precipitation should be carefully controlled. The temperature for the precipitation is preferably in the range of from about 20° C. to about 100° C. preferably from about 50° C. to about 85° C. and the pH during the precipitation process is maintained between about 5.5 and about 7.5, preferably between about 6.0 to about 7.0 and more preferably, between about 6.3 and about 6.7. The precipitating agent will be an alkali metal or an ammonium carbonate solution. The precipitate thus obtained is a mixture of carbonates, basic carbonates, oxides, hydrated oxides and hydroxides. The precipitate is washed, preferably several times with water, aged, reslurried and then dried and calcined, preferably in air at a temperature of from about 200° C. to about 400° C., with a temperature of about 250° C. to about 350° C. being preferred. The drying is carried out at a temperature sufficient to remove the water. This step is conveniently combined with the calcination by a suitable ramping of the temperature from room temperature slowly through the drying temperature, then up to calcination temperature. The calcined material is shaped, for example, by pelleting under pressure using alumina as a binder, or graphite as lubricant. The oxide mixture is pretreated in a hydrogen-containing atmosphere prior to use as a catalyst to bring it to its most active state. Pretreatment is accomplished by contacting the catalyst with a stream of hydrogen, or of hydrogen mixed with an inert gas or diluent at a temperature ranging from about 100° C. to about 400° C. Suitable diluent gases for the activating gas mixture include nitrogen, the noble gases and mixtures thereof.

In addition it has been discovered in the present invention that it is preferable to sinter the catalyst before use at a temperature of about 800–10000° C., preferably about 900–960° C.

In a preferred embodiment, an aqueous solution of copper, zinc and zirconium salts is employed. Preferably utilized are copper nitrate, zinc nitrate, and zirconium nitrate. A second solution of alkali metal or preferably, ammonium carbonate is prepared. The two solutions are heated to a temperature of about 20° C. to about 85° C. and simultaneously metered into the precipitation container at rates such that the pH in the precipitation container is maintained between 5.5 and 7.5. Additional water may be used either initially in the precipitation container or added concurrently with the salt solution and precipitation solution. The resulting precipitate is thoroughly washed, dried, calcined at about 300° C. and activated in hydrogen at temperatures ranging from about 100° C. to about 400° C.

One of the exemplified catalysts of the present invention (Examples 1 and 7–9) which provides good selectivity, while avoiding problems with toxicity and metallurgic concerns is prepared in the form of mixed carbonates of copper, zinc, and zirconium. The catalyst is used in an amount of from about 0.05 wt % to 25 wt %, based on the alkali aromatic monocarboxylate used as the starting material, but may also be used in larger amounts.

In a second embodiment the catalyst comprises basic copper, optionally employed with an alkali metal promoter. When only copper (II) is used, the catalyst is treated with a base. A specific examples comprises a copper (II)-based catalyst treated with preferably potassium hydroxide, and optionally used in conjunction with a cesium carbonate or potassium carbonate promoter. The catalyst is prepared by heating one mole of basic copper carbonate $CUCO_3.Cu(OH)_2$ with two moles of KOH. The two solids are first mixed in an electric mill under an inert atmosphere. The solid mixture is then heated to at least 175° C., under vacuum for several hours. The key preparative step in making the copper (II) carbonate catalyst of the present invention is allowing basic copper carbonate to react with potassium hydroxide at temperatures above 175° C. Without the KOH, the basic copper carbonate acts to decarboxylate potassium naphthoate, as shown in Example 10.

The catalyst may be uniformly and finely distributed throughout the reaction mixture by transforming an aqueous solution of the salts serving as the starting material, which has the catalyst dissolved or suspended therein, into a dry powder.

In U.S. Pat. No. 3,766,258, a catalyst composition is disclosed which comprises basic copper carbonate, cadmium fluoride and potassium carbonate. In the examples, however, a water extraction and subsequent acidification/filtration isolate the products. No analytical technique is disclosed, and it is likely that unreacted KNA is mistakenly counted as diacid product. In contrast, the present invention avoids the use of cadmium fluoride and the associated concerns with extreme toxicity and reactor corrosion.

The following examples will further illustrate the present invention and enable others skilled in the art to understand the invention more completely. It is to be understood that these examples are given only for the purpose of illustration and explanation and should not be construed as limiting the invention in any way.

EXAMPLE 1

This example demonstrates the preparation of the mixed metal carbonate catalysts of this invention. The mixed metal carbonates were made by preparing a solution of mixed nitrates consisting of 96 grams (0.41 mole) of cupric nitrate, 60 grams (0.2 mole) zinc nitrate, 3.0 grams (0.008 mole) zirconyl nitrate in one liter of water, heating to 85° C., and placing in a dish and funnel. In a second funnel was placed a hot (50° C.) 1.0 molar solution of ammonium carbonate of sufficient quantity to provide a molar excess over the metal nitrates. The two solutions were added simultaneously over a period of about 20 minutes to a vessel containing 1 liter of vigorously stirred water at 65° C. The rates of addition were adjusted so as to maintain the pH of the mixture at about 6.5. After the addition was completed, the slurry was aged at 85° C. for 20 minutes and then allowed to settle after which it was washed 5 times by decantation and reslurrying before being filtered and dried at 125° C. for 16 hours. The metal content is approximately: $Cu_{0.41}$, $Zn_{0.2}$, $Zr_{0.005}$.

The catalyst of the present invention is prepared from the mixed metal nitrates by sintering a 12 gram mixture of Cu (II), Zn, and Zr carbonates for 2 hours at approximately 900–960° C. The resulting black powder was removed from the oven and stored in a dry box. The carbonate mixture used in Comparative Example 10 was not sintered and resulted in a low yield and significant decarboxylation.

EXAMPLE 2

Example 2 demonstrates the preparation of a catalyst containing lanthanum. A solution of mixed nitrates, 96 grams (0.41 mole) of cupric nitrate, 60 grams (0.2 mole) zinc nitrate, 3.3 grams (0.008 mole) lanthanum nitrate in one liter of water was heated to 85° C. and placed in a dish and funnel. In a second funnel was placed a hot 50° C. 1 molar solution of ammonium carbonate of sufficient quantity to provide an excess over the metal nitrates. Two solutions were added simultaneously over a period of about 20 minutes to a vessel containing 1 liter of vigorously stirred distilled water at 65° C. The rates of addition were adjusted so as to maintain the pH of the mixture at about pH equal to about 6.5. After the addition had been completed the slurry was aged at 85° C. for 20 minutes and then allowed to settle and washed 5 times by decantation and reslurrying before being filtered and dried. The mixed carbonates were dried and then sintered at 900–960° C. for 4 hours. The resulting oxide material was compressed isostatically at 20,000 lbs. and then crushed and sieved.

EXAMPLE 3

The catalyst preparation procedure for Example 1 was followed, except that 3.47 g (0.008 mole) cerous nitrate was utilized in place of the lanthanum nitrate.

EXAMPLE 4

The catalyst preparation procedure for Example 2 was followed, except that 3.00 g (0.008 mole) zirconyl nitrate was used in place of the lanthanum nitrate.

EXAMPLE 5

The catalyst preparation procedure for Example 1 was followed, except that 2.2 g (0.009 mole) magnesium nitrate hexahydrate was added to the nitrate salt solution.

EXAMPLE 6

A Cu/Zn/Zr catalyst was prepared as in Example 1, the catalyst was then mixed with 10% by weight of Catapal D alumina (marketed by Vista Chemical Corporation) and a small amount of acetic acid as a peptizing agent. The mixture was mulled, then extruded and calcined as described in Example 1.

EXAMPLE 7

The catalyst preparation procedure for Example 1 was followed, except that 120 g (0.55 moles) copper nitrate was used, and the lanthanum nitrate as replaced with 12.0 g (0.3 moles) aluminum nitrate nonahydrate.

EXAMPLES 8–10

Examples 8 through 10 demonstrate the invention comprising the use of the Cu (II), Zn, Zr carbonates in a disproportionation reaction. In a dry box, 2.7 g of catalyst was combined with 1.0 g $K_2CO_3$ and 5 g potassium 2-naphthoate. This solid composition was milled to a fine powder and loaded into a rotating autoclave. The autoclave was filled with 250 psig $CO_2$ and allowed to rotate within an oven. The oven temperature was 450° C. The residence time was approximately 30 minutes. The resulting product was a dark brown solid.

The products were analyzed by proton NMR spectroscopy by taking the crude reaction product and digesting it in hot $D_2O$/KOH that dissolved the mono- and diacid salts. The soluble fraction was filtered and analyzed. In a separate NMR experiment, naphthalene is analyzed by digesting the crude run product in DMSO, which preferentially dissolves naphthalene. Using appropriate internal standards for quantification, the following was determined:

TABLE I

| Run No. | Conditions and Run Time | Catalyst/ reactants | Yield Naphthalene | Yield 2,6-K2NDA | Selectivity 2,6 K2NDA |
|---|---|---|---|---|---|
| Ex. 8 | 450° C./30 min. | 900° C.; Sintered Cu/Zn/Zr carbonates $K_2CO_3$, K2NA | 111% | 75% | 85.4% |
| Ex. 9 | 450° C./30 min. | Same as 176-1, but no $K_2CO_3$ added | 102% | 68% | 70% |
| Ex. 10 | 450° C./30 min. | Catalyst not sintered | 170% decarboxylation | Trace Detected | NA |

EXAMPLE 11

Example 11 demonstrates the preparation of the copper (II) carbonate catalyst. The catalyst is prepared by heating one mole of basic copper carbonate [$CuCO_3 \cdot Cu(OH)_2$] with 2 moles of KOH. The two solids are first mixed in an electric mill under an inert atmosphere. The solid mixture is then heated to at least 175° C. under vacuum for several hours. The resulting black powder was removed from the oven and stored in a dry box.

EXAMPLES 12–16

In Examples 12 through 16, the catalyst prepared in Example 11 was used in a disproportionation reaction. The disproportionation reaction using the copper (II) catalyst of Example 11 was carried out in the following manner:

In a dry box, 2.7 g of catalyst was combined with 1.0 g alkali metal carbonate (K or Cs) and 5 g potassium 2-naphthoate. The reaction mixture next was milled to a fine powder and loaded into an autoclave. The autoclave was filled with 250 psig $CO_2$ and then heated. For run 181B, the same reaction mixture was put into an autoclave and rotated. The reaction conditions are noted in Table II. The resulting product was a dark brown solid.

The products were analyzed by proton NMR spectroscopy by taking the crude reaction product and digesting in hot $D_2O$/KOH which dissolved the mono- and diacid salts. The soluble fraction was filtered and analyzed. In a separate NMR experiment, naphthalene is analyzed by digesting the crude run product in DMSO, which preferentially dissolves naphthalene. Using appropriate internal standards for quantification, the results were noted and recorded in Table II.

TABLE II

| Run No. | Conditions and Run Time | Catalyst/ reactants | Yield Naphthalene | Yield 2,6-K2NDA | Selectivity 2,6 K2NDA |
|---|---|---|---|---|---|
| Ex. 12 | 425° C./1 Hour | $CuCO_3 \cdot Cu(OH)_2$/ $Cs_2CO_3$/K2NA | 100% | 68% | 80% |
| Ex. 13 | 425° C./1 Hour | $CuCO_3 \cdot Cu(OH)_2$/ $Cs_2CO_3$/K2NA | 86% | 45% | 3% |
| Ex. 14 | 450° C./1 Hour | $CuCO_3 \cdot Cu(OH)_2$/ $Cs_2CO_3$/K2NA | 78% | 50% | 100%, no other isomer detected by NMR |
| Ex. 15 | 425° C./1 Hour | $CuCO_3 \cdot Cu(OH)_2$/ No Carbonate/ KNA | 50% | 58% | 3% |
| Ex. 16 | 425° C./1 Hour | $CuCO_3 \cdot Cu(OH)_2$/ $K_2CO_3$/K2NA | 161% decarboxylation | 5% | 0% |

We claim:

1. In a process for the disproportionation/isomerization of aromatic carboxylic acid salts by introducing an alkali metal salt of an aromatic carboxylic acid into a disproportionation zone at elevated temperature and high pressure in the presence of a disproportionation catalyst, the improvement comprising the use of a halide-free disproportionation/isomerization catalyst comprising a copper compound, a zinc compound, and at least one compound selected from the group consisting of aluminum, zirconium, magnesium, a rare earth, and mixtures thereof.

2. The process of claim 1 wherein said catalyst contains from about 10 percent by weight to about 80 percent by weight, calculated as the oxide, basis the total weight of the catalyst, of copper.

3. The process of claim 1 wherein said catalyst contains from about 10 percent by weight to about 80 percent by weight, calculated as oxide, basis the total weight of the catalyst, of zinc.

4. The process of claim 1 wherein said catalyst contains copper, zinc, and zirconium.

5. The process of claim 4 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst of zirconium.

6. The process of claim 1 wherein said catalyst contains copper, zinc and a rare earth compound.

7. The process of claim 6 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.1 percent by weight to about 20 percent by weight, calculated as the oxide, basis the total weight of the catalyst, of rare earth.

8. The process of claim 6 wherein said rare earth is selected from the group consisting of praseodymium, neodymium, yttrium, lanthanum, samarium, thorium, cerium, and mixtures thereof.

9. The process of claim 6 wherein said rare earth is lanthanum.

10. The process of claim 6 wherein said rare earth is cerium.

11. The process of claim 1 wherein said catalyst contains copper, zinc, and aluminum.

12. The process of claim 11 wherein said catalyst contains from about 10 percent by weight to about 80 percent by weight, calculated as the oxide, basis the total weight of the catalyst, of copper. From about 10 percent by weight to about 80 percent by weight, calculated as the oxide, basis the total weight of the catalyst, of zinc, and from about 0.05 percent by weight to about 30 percent by weight, basis the total weight of the catalyst, of aluminum.

13. The process of claim 1 wherein said catalyst contains copper, zinc, zirconium and aluminum.

14. The process of claim 13 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of zirconium, and from about 0.05 percent by weight to about 30 percent by weight, basis the total weight of the catalyst, of aluminum.

15. The process of claim 1 wherein said catalyst contains copper, zinc, magnesium and a rare earth compound.

16. The process of claim 15 wherein said catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of magnesium, and from about 0.1 percent by weight to about 20 percent by weight, calculated as the oxide, basis the total weight of the catalyst, of rare earth.

17. The process of claim 16 wherein said rare earth is selected from the group consisting of selected from the group consisting of praseodymium, neodymium, yttrium, lanthanum, samarium, thorium, cerium and mixtures thereof.

18. The catalyst of claim 4 wherein the catalyst comprises copper (II) carbonate, zinc carbonate, and zirconium carbonate.

19. The catalyst of claim 1 further comprising only copper carbonate, and no zinc compound, treated with a base, and optionally used with a promoter.

20. The catalyst of claim 19 comprising copper (II) carbonate treated with potassium hydroxide, optionally used with a promoter.

21. The catalyst of claim 20 wherein a promoter is used in an amount of about 5 to 25 of the total weight of the catalyst and is selected from the group consisting of $Cs_2CO_3$, $K_2CO_3$.

22. The catalyst of claim 21 wherein the promoter is cesium carbonate.

23. A copper (II) carbonate catalyst prepared by heating basic copper (II) carbonate, $[CuCO_3.Cu(OH)_2]$ with potassium hydroxide in a molar ratio of about 1:2, mixing in an electric mill under inert atmosphere, and heating to at least 175° C. under vacuum.

24. In a process for disproportionation/isomerization of aromatic carboxylic acid salts characterized by reacting said aromatic carboxylic acid salt at a temperature of from about 300–600° C. and 700 to 1000 psi $CO_2$, in the presence of a disproportionation catalyst, the improvement of using as the disproportionation catalyst a halide-free catalyst comprising copper (II) carbonate, zinc carbonate, and zirconium carbonate.

25. In a process for disproportionation/isomerization of aromatic carboxylic acid salts characterized by reacting said aromatic carboxylic acid salt at a temperature of from about 300–600° C. and 700 to 1000 psi $CO_2$ in the presence of a disproportionation catalyst, the improvement comprising using as a disproportionation catalyst a halide-free catalyst comprising copper (II) carbonate treated with potassium hydroxide, optionally using a promoter selected from cesium or potassium carbonate.

* * * * *